(12) United States Patent
Linnell et al.

(10) Patent No.: US 10,453,323 B2
(45) Date of Patent: Oct. 22, 2019

(54) REMOTE NOTIFICATION SYSTEM FOR MEDICAL DEVICES

(71) Applicants: John Jeffrey Linnell, Fountain Valley, CA (US); Mark Anthony Hastings, Blue Springs, MO (US)

(72) Inventors: John Jeffrey Linnell, Fountain Valley, CA (US); Mark Anthony Hastings, Blue Springs, MO (US)

( * ) Notice: Subject to any disclaimer, the term of this patent is extended or adjusted under 35 U.S.C. 154(b) by 0 days.

(21) Appl. No.: 16/397,721

(22) Filed: Apr. 29, 2019

(65) Prior Publication Data

US 2019/0261068 A1 Aug. 22, 2019

Related U.S. Application Data

(63) Continuation-in-part of application No. 15/423,258, filed on Feb. 2, 2017, now Pat. No. 10,276,038.

(60) Provisional application No. 62/310,518, filed on Mar. 18, 2016.

(51) Int. Cl.
| | |
|---|---|
| *G08B 21/00* | (2006.01) |
| *G08B 21/02* | (2006.01) |
| *H04L 29/08* | (2006.01) |
| *G08C 17/02* | (2006.01) |
| *H04W 4/02* | (2018.01) |

(52) U.S. Cl.
CPC ...... *G08B 21/0211* (2013.01); *G08B 21/0283* (2013.01); *G08B 21/0294* (2013.01); *G08C 17/02* (2013.01); *H04L 67/12* (2013.01); *H04L 67/18* (2013.01); *H04L 67/22* (2013.01); *H04W 4/02* (2013.01)

(58) Field of Classification Search
None
See application file for complete search history.

(56) References Cited

U.S. PATENT DOCUMENTS

| | | | |
|---|---|---|---|
| 2016/0091196 A1* | 3/2016 | Chien | F21V 33/0048 362/253 |
| 2016/0097522 A1* | 4/2016 | Chien | F21V 33/00 362/183 |
| 2016/0134737 A1* | 5/2016 | Pulletikurty | G06F 3/0227 715/735 |
| 2016/0156207 A1* | 6/2016 | Frankenberger | H02J 7/0027 320/101 |
| 2016/0235981 A1* | 8/2016 | Southwell | A61N 1/22 |
| 2016/0373457 A1* | 12/2016 | Matson | H04L 67/306 |
| 2018/0131847 A1* | 5/2018 | Kokonaski | H02J 7/0044 |

* cited by examiner

*Primary Examiner* — Julie B Lieu
(74) *Attorney, Agent, or Firm* — RC Trademark Company (57) ABSTRACT

A power monitoring device for monitoring power-up events and power-down events comprises a processor, a power change detector to detect power changes in a host device, a logger to record a log of power changes detected by the power change detector in the host device, and a transceiver to transmit the log to a monitoring system. The power change detector monitors power being drawn by the host device based on at least one of (i) detecting power usage through an exterior of a power cord electrically coupled to the host device, (ii) receiving an image from a camera aimed at a control panel of the host device where power usage is detected based on a visual change in the received image, (iii) monitoring vibration of the host device or (iv) sound emitted by the host device.

20 Claims, 12 Drawing Sheets

Receive an indication of a power-up event associated with a host device via a power change detector that is external to the host device
1202

Receive an indication of a power-down event associated with the host device via the power change detector that is external to the host device
1204

Record the indication of the power-up event in a log file
1206

Record the indication of the power-down event in the log file
1208

Transmit information from the log file to a monitoring system.
1210

REMOTE NOTIFICATION SYSTEM FOR MEDICAL DEVICES

The current application claims priority to the U.S. Provisional Patent application Ser. No. 62/310,518 filed on Mar. 18, 2016 and U.S. patent application Ser. No. 15/423,258 filed on Feb. 2, 2017.

FIELD OF THE INVENTION

The present invention relates generally to monitoring medical devices. More specifically, the present invention provides a monitoring device for monitoring a medical device remotely and alerting a user of undesirable states.

BACKGROUND OF THE INVENTION

Negative pressure wound therapy (NPWT) is a medical technique which induces healing through application of a vacuum to a wound through a sealed dressing. With this, sealed wound dressings connect to a vacuum pump to control the application of sub atmospheric pressure. NPWT units may be used in medical centers (hospitals, doctor's offices, etc.), however, it is common for them to be used inside of homes. In general, healthcare professionals diagnose alerts produced by NPWT units over the phone when it is late. This technique is only somewhat effective, as communication errors often occur, thus producing additional problems and confusion. Because of this, inventors have developed NPWT units and other medical devices which alert healthcare professionals from remote locations, however, there such inventions lack the output of several important alerts necessary to keep everything running smoothly for extended periods of time.

It is therefore an objective of the present invention to introduce a remote notification system for a negative pressure wound therapy unit. The present invention utilizes an NPWT unit capable of sending wireless notifications to an online dashboard application which may be accessed in remote locations, via a wireless network. Alerts which appear on the NPWT unit will be relayed to an internal microcontroller and transmitted out to the corresponding dashboard application which may be accessed on a remote computing device, such as a laptop or smartphone. Upon logging into the dashboard application, users will be able to diagnose the alert and figure out the proper course of action. The dashboard application will give full remote access to the NPWT unit, allowing users to troubleshoot and track any potential problems which may occur from a far. Additionally, the system allows for better overall safety of patients and in total, bettering the overall continuum of care within the home health and long term care markets. While the preferred embodiment is intended to be used with a NPWT unit, it is an object of the present invention to provide a device that can be used in any medical device.

DETAIL DESCRIPTIONS OF THE INVENTION

All illustrations of the drawings are for the purpose of describing selected versions of the present invention and are not intended to limit the scope of the present invention.

Figure 1:
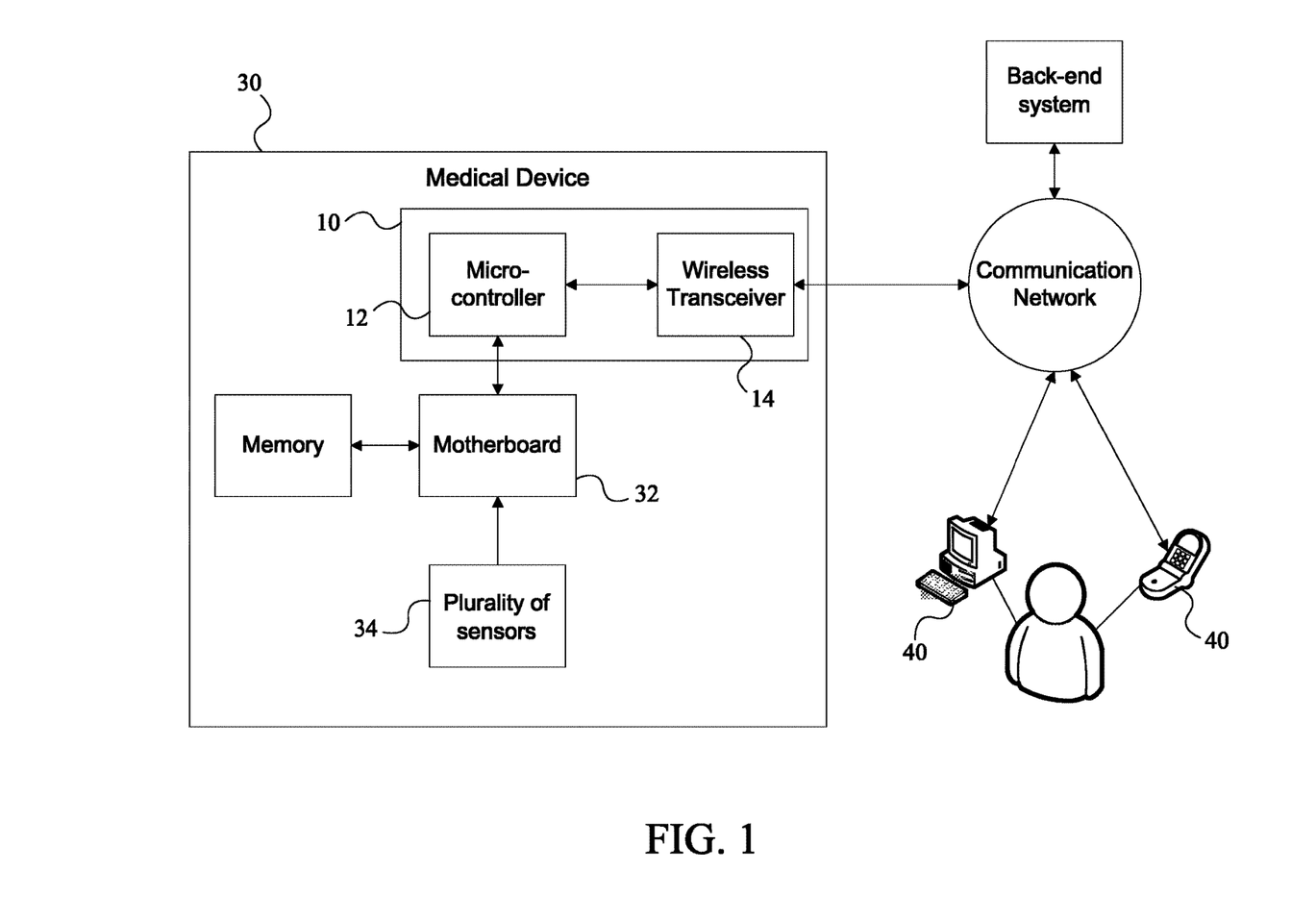
FIG. 1 is a diagram depicting the communication between the medical device and the remote computing device via the monitoring device, using a wireless communication network.

The present invention is a monitoring device 10 that serves as a remote notification system and provides communication between a medical device 30 and a remote computing device 40. The monitoring device 10 may be integrated into the medical device 30 as depicted in FIG. 1, such that the monitoring device 10 can monitor the medical device 30 and monitor various parameters and states of the medical device 30. Data collected from the medical device 30 is displayed on the remote computing device 40 through a dashboard application, wherein the commands can also be sent to the medical device 30 via the dashboard application. The dashboard application can be hosted by a back-end system, rooted on the remote computing device 40, or a combination thereof.

The remote computing device 40 is any electronic device that is capable of wirelessly communicating with at least one transceiver 14 of the monitoring device 10. For example, the remote computing device 40 can be a laptop, smartphone, or tablet. In reference to FIG. 4, the monitoring device 10 may be installed in, or external to, and synchronized with the medical device 30, such that data can be transferred between a microcontroller 12 from the monitoring device 10 and a main board 32 of the medical device 30. Examples of the medical device 30 include a negative pressure wound therapy (NPWT) unit, an enteral feeding pump, an infusion pump, a compression pump, a ventilator, or a continuous positive airway pressure (CPAP) pump.

While the present invention is hereinafter described in conjunction with the medical device 30 being a NPWT unit, it is to be understood that the present invention is not limited in its application to the details of the components and arrangements as described or illustrated. The present invention is capable of other embodiments and of being utilized and carried out in various ways not explicitly described herein but that can be reasonably conjectured within the scope of an electrical device and/or medical devices. It is also to be understood that the phrasing and terminology employed herein are for the purpose of description and should not be regarded as limiting.

The present invention allows the medical device 30 to be utilized in homes, medical centers, etc., while allowing caregivers, nursing assistants, doctors, etc. the ability to remotely access and monitor the medical device 30. This can be used to remotely troubleshoot issues that a patient may be having with the medical device 30 or to provide assurance that a patient or caregiver is properly adhering to parameters set forth by a doctor, such as changing dressings on time or using the therapy for the required hours in a day. The remote access can also be used to notify parties, such as the medical center or a manufacturer, when general maintenance on the medical device 30 is required.

Figure 2:
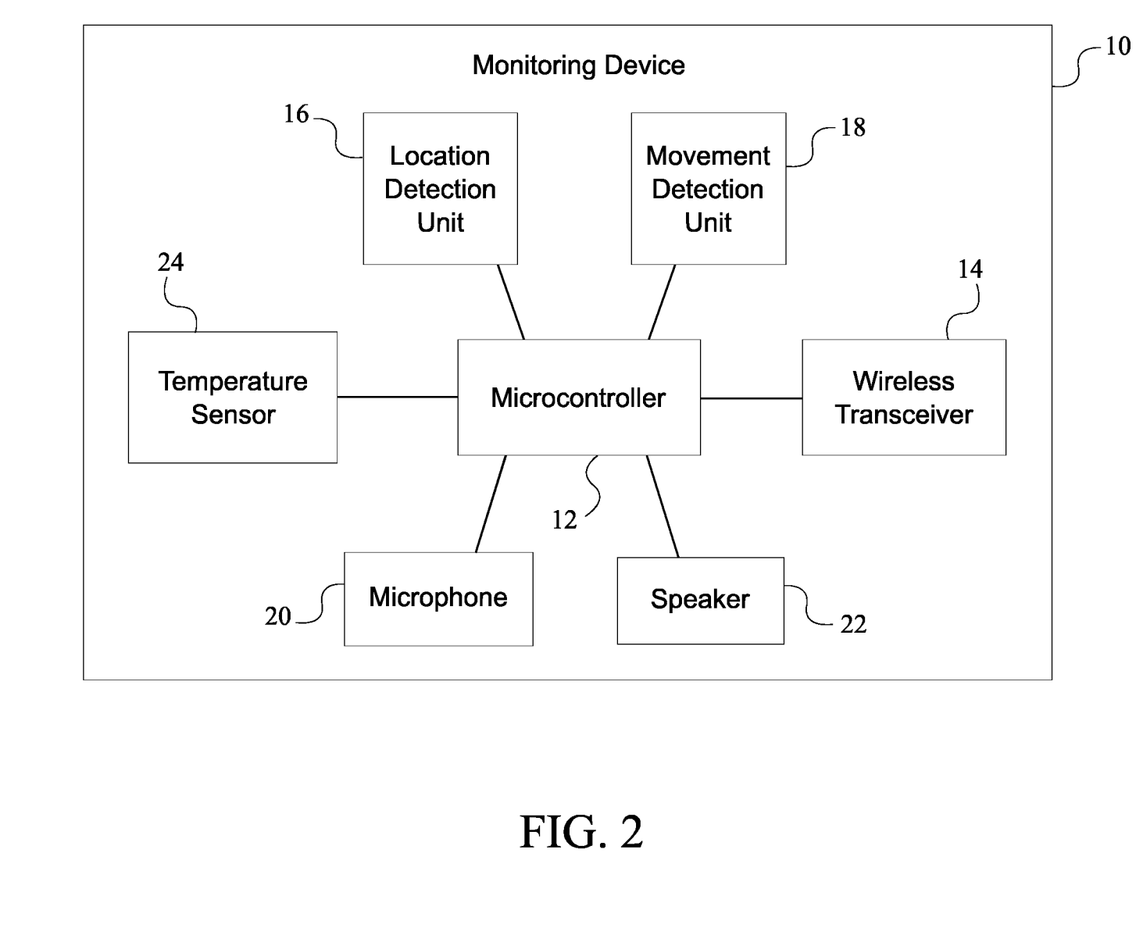
FIG. 2 is a diagram depicting the electrical connections between the microcontroller and the other components of the monitoring device.

In reference to FIG. 2, in addition to the microcontroller 12 and the transceiver 14 previously mentioned, the monitoring device 10 may include a location detection unit 16, a motion detection unit 18, a temperature sensor 24, a microphone 20, and a speaker 22. The microcontroller 12, the transceiver 14, the location detection unit 16, the motion detection unit 18, and the temperature sensor 24 are configured to be operably disposed within or external to the medical device 30, wherein the microcontroller 12, the transceiver 14, the location detection unit 16, the motion detection unit 18, and the temperature sensor 24 may be mounted as one unit or standalone. The microphone 20 and the speaker 22 may be positioned within or external to the medical device 30.

The microcontroller 12 provides a processing unit that is configured to send and receive signals with the main board 32, and may additionally have a storage device to save predetermined commands and settings. The main board 32 is a motherboard, or other similar device, that controls the operations of the medical device 30 and communicates with a plurality of sensors 34 of the medical device 30. The microcontroller 12 is configured to be communicably coupled to the main board 32 either wirelessly or through a wired connection.

Figure 4:
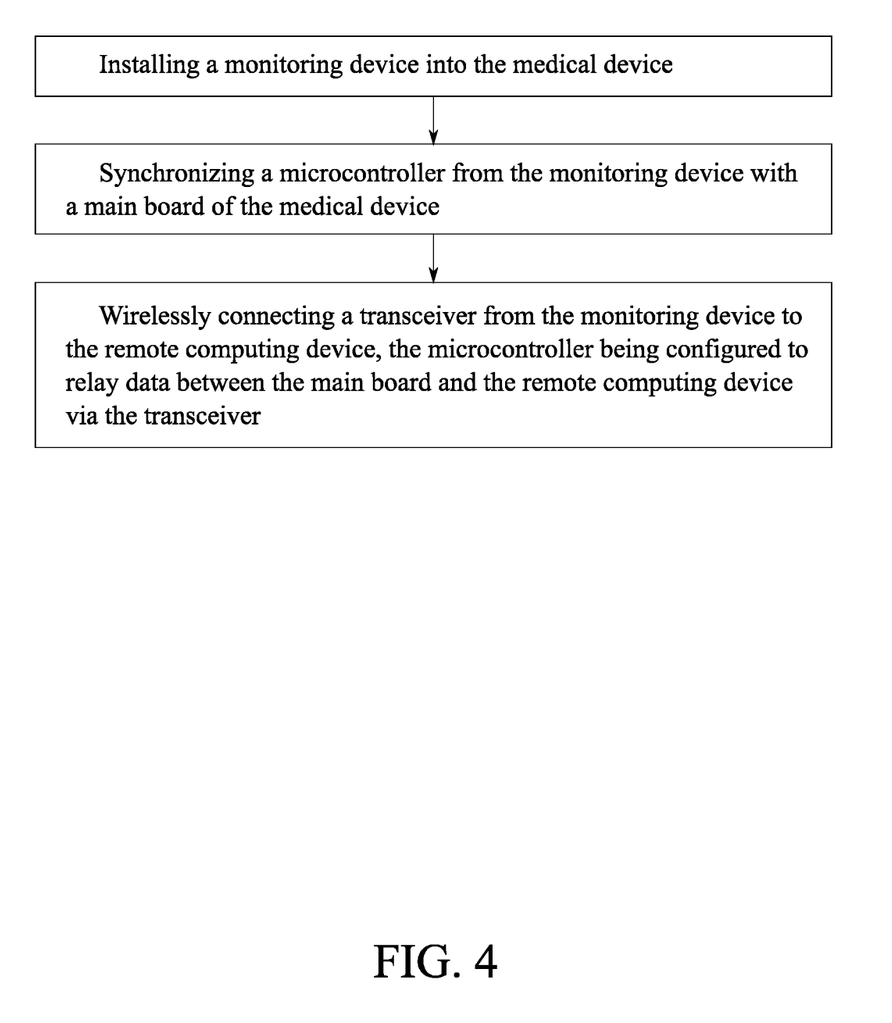
FIG. 4 is a flowchart depicting the steps for monitoring the medical device to communicate with the remote computing device via the monitoring device.

In reference to FIG. 4, the monitoring device 10 is first installed within or external to the medical device 30, and the microcontroller 12 then is synchronized with the main board 32, either through a wireless or wired connection. The microcontroller 12 is coded to communicate back and forth with the main board 32, such that the microcontroller 12 is able to monitor the main board 32. Once the microcontroller 12 is synchronized with the main board 32, the transceiver 14 is wirelessly connected to the remote computing device 40. The transceiver 14 is electrically connected to the microcontroller 12 as depicted in FIG. 2, such that the microcontroller 12 can relay data between the main board 32 and the remote computing device 40 via the transceiver 14.

Figure 10:
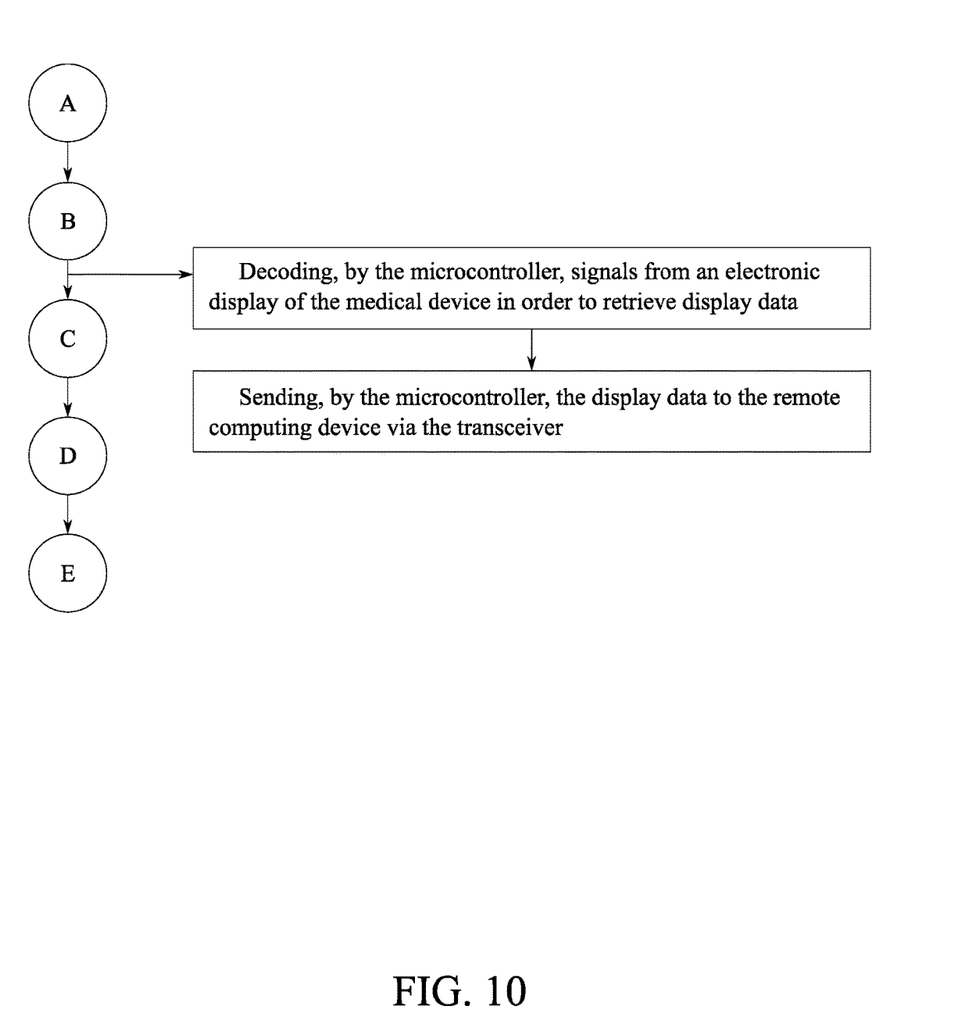
FIG. 10 is a flowchart thereof, further depicting steps for retrieving information from an electronic display of the medical device.

Furthermore, the microcontroller 12 is electronically connected to an electronic display of the medical device 30. In reference to FIG. 10, the microcontroller 12 is configured to decode signals from the electronic display in order to retrieve display data, wherein the microcontroller 12 can then relay the display data to the remote computing device 40 via the transceiver 14. The display data may include sensor readings, power states, medical alerts, or any other pertinent information that the electronic display is configured to present to a user. It is possible for the microcontroller 12 to be directly wired to the electronic display, or indirectly via the main board 32. The electronic display can be any type of display interface, such as a liquid crystal display (LCD) screen or a light emitting diode (LED) screen.

Figure 3:
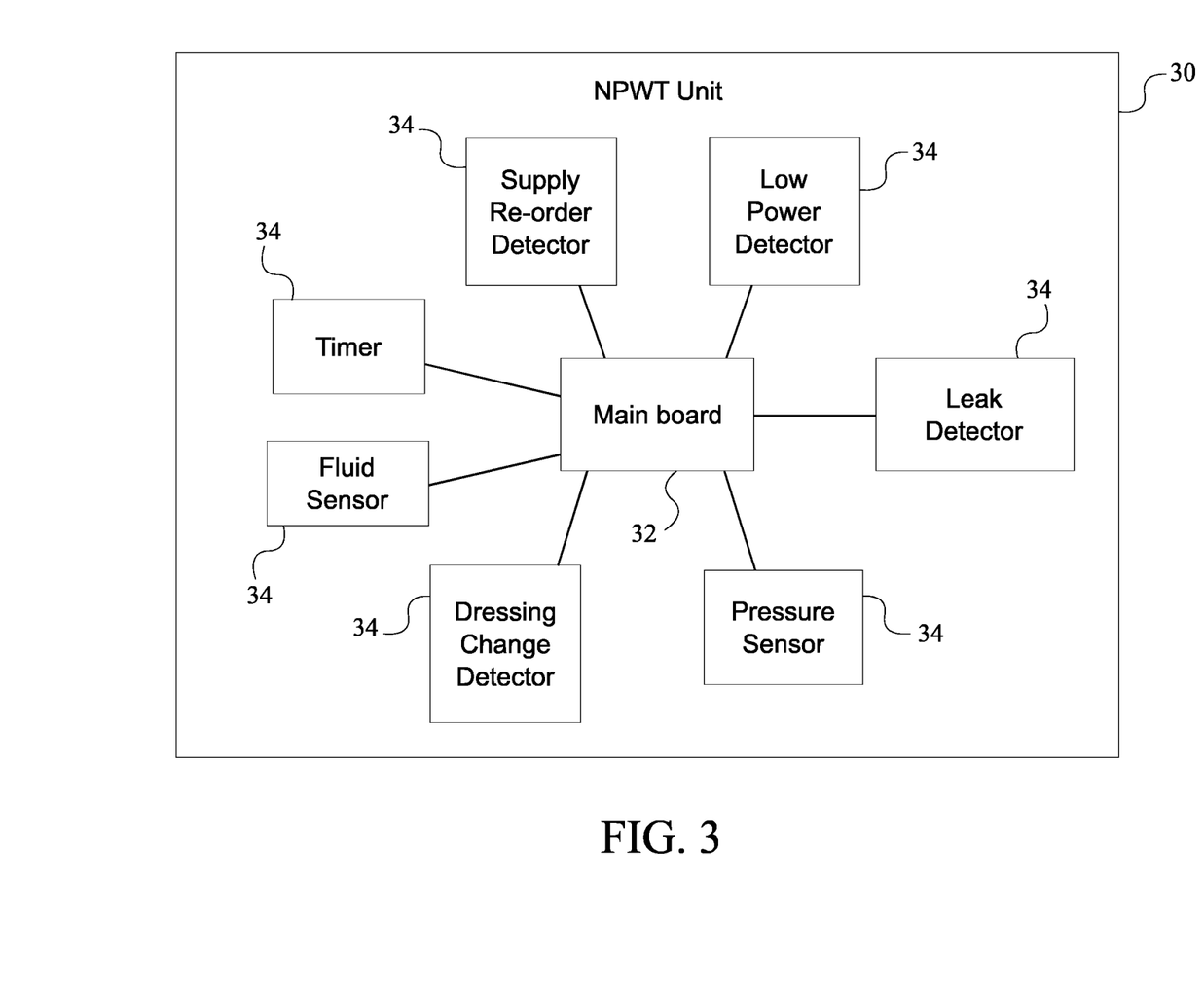
FIG. 3 is a diagram depicting exemplary implementations of the plurality of sensors, wherein the medical device is a negative pressure wound therapy unit.
Figure 5:
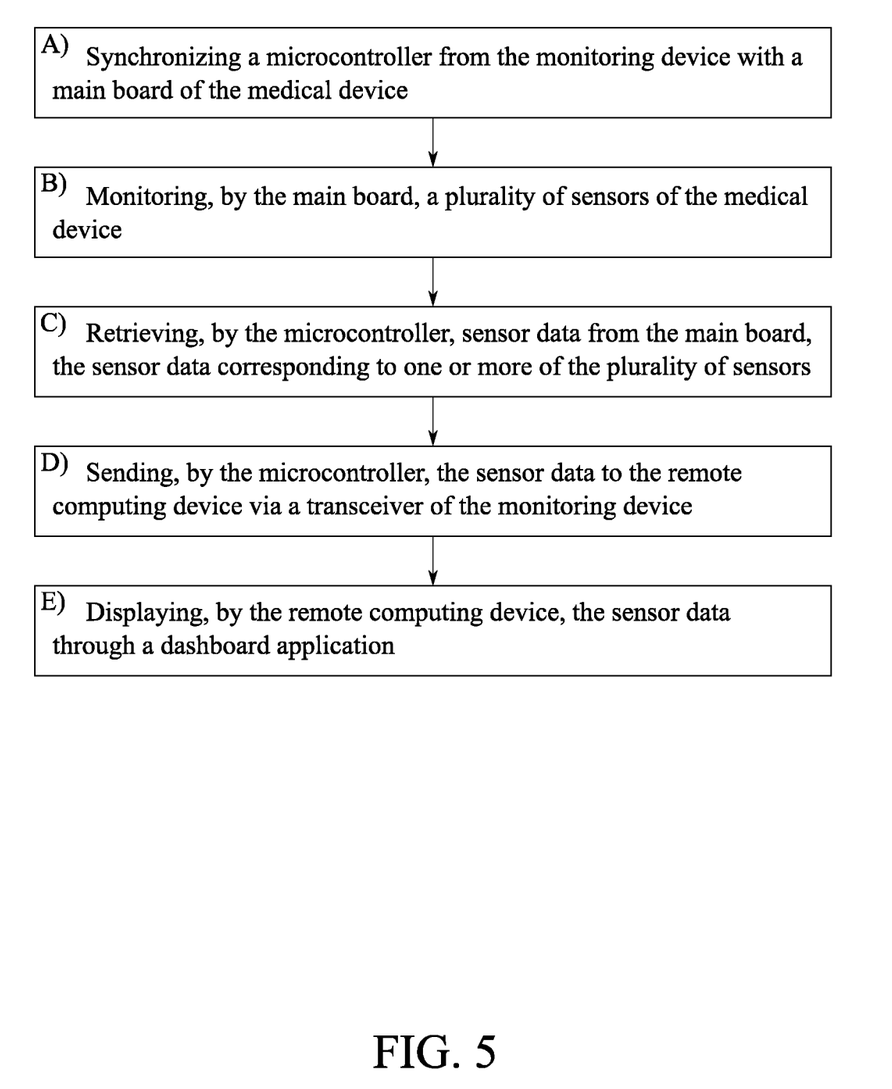
FIG. 5 is a flowchart depicting steps for retrieving data from the medical device and displaying the data to a user through the dashboard application.

In reference to FIG. 5, the main board 32 monitors the plurality of sensors 34 to ensure that the proper medical treatment is being provided. In reference to FIG. 3, for a NPWT unit, the plurality of sensors 34 may include a leak detector, a fluid sensor, a low power detector, and a pressure sensor. The plurality of sensors 34 collects sensor data which is sent to the main board 32 and stored in memory; the sensor data corresponding to one or more of the plurality of sensors 34. The microcontroller 12 can then retrieve the sensor data from the main board 32 and send the sensor data to the remote computing device 40 via the transceiver 14. The sensor data may be preprocessed by the main board 32, processed by the microcontroller 12, or a combination thereof.

In further reference to FIG. 5, the sensor data is sent to the remote computing device 40 via a telecommunication network, internet network, or similar wireless network. The remote computing device 40 can then display the sensor data through the dashboard application. The dashboard application may depict the sensor data using charts, graphs, or anything or desirably means of visually presenting the sensor data to the user.

In order to access the dashboard application, a user must be registered with the back-end system that supports the dashboard application and must have a unique identifier and a password. When opening the dashboard application, the user is presented with a login portal, wherein the user is prompted to enter the unique identifier and the password to gain access to the user interface of the dashboard application. Once logged in the user can remotely monitor the medical device 30 and retrieve the desired sensor data through the remote computing device 40. The features accessible through the dashboard application may vary depending on the user. For example, a user account for a doctor may be given more privileges than the user account of a patient.

The dashboard application can be used by the user to remotely monitor one or more of a plurality of medical device 30 functions. Commands can be entered through the user interface of the dashboard application or through voice commands dictated to the remote computing device 40. Once a command has been sent to the microcontroller 12 and carried out by either the microcontroller 12 or the main board 32, the user interface is updated accordingly or may receive an audial confirmation of the command.

Alternative to using the dashboard application, the microphone 20 may be used by the user to monitor the plurality of medical device 30 functions. The microphone 20 is electrically connected to the microcontroller 12, such that audial signal picked up by the microphone 20 are relayed to the microcontroller 12. The audial signals are then processed by the microcontroller 12. The speaker 22, which is electrically connected to the microcontroller 12, can then be used to provide an audial confirmation that the desired function has been carried out.

Figure 9:
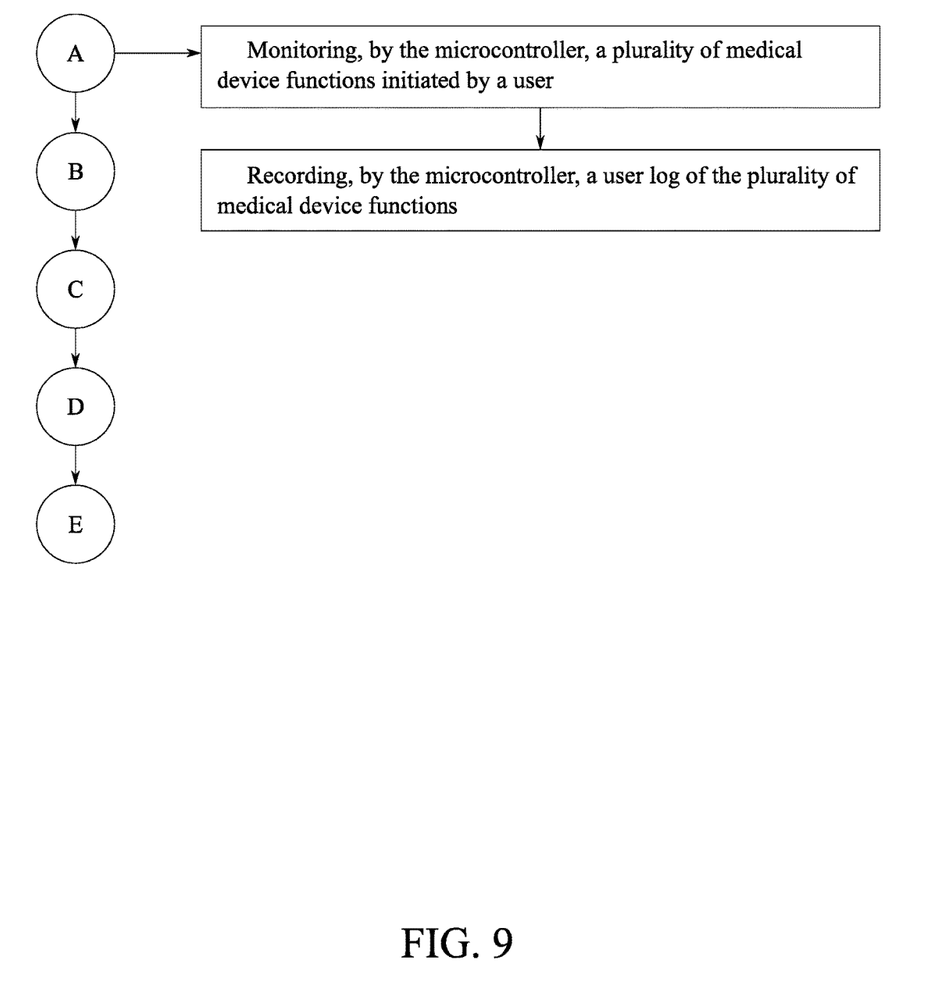
FIG. 9 is a flowchart thereof, further depicting steps for recording a user log of functions initiated on the medical device by a user.

In reference to FIG. 9, through all methods of input, the microcontroller 12 monitors the plurality of medical device 30 functions initiated by the user and records a user log of the plurality of medical device 30 functions. In this way, the present invention can be used by doctors or other medical officials to monitor patient compliance and ensure that the medical device 30 is being used properly. The user log may additionally be used to record how long the medical device 30 has been used, when the medical device 30 is turned on or off, reset, or receives other collected data from one or more sensors.

The microcontroller 12 also provides the ability to send alerts and notifications to the remote computing device 40 if an undesirable state is determined by the microcontroller 12. The alerts are sent from the microcontroller 12 to the remote computing device 40 over a wireless communication network. The alerts may be sent to the remote computing device 40 through the dashboard application, sent as an email, sent as a short message service (SMS) notification, or sent using any other desirable wireless standard. If the alerts are sent to through the dashboard application, the remote communication device will signal that an alert has been received and the user must then log into the dashboard application in order to view the full details of the alert.

Figure 6:
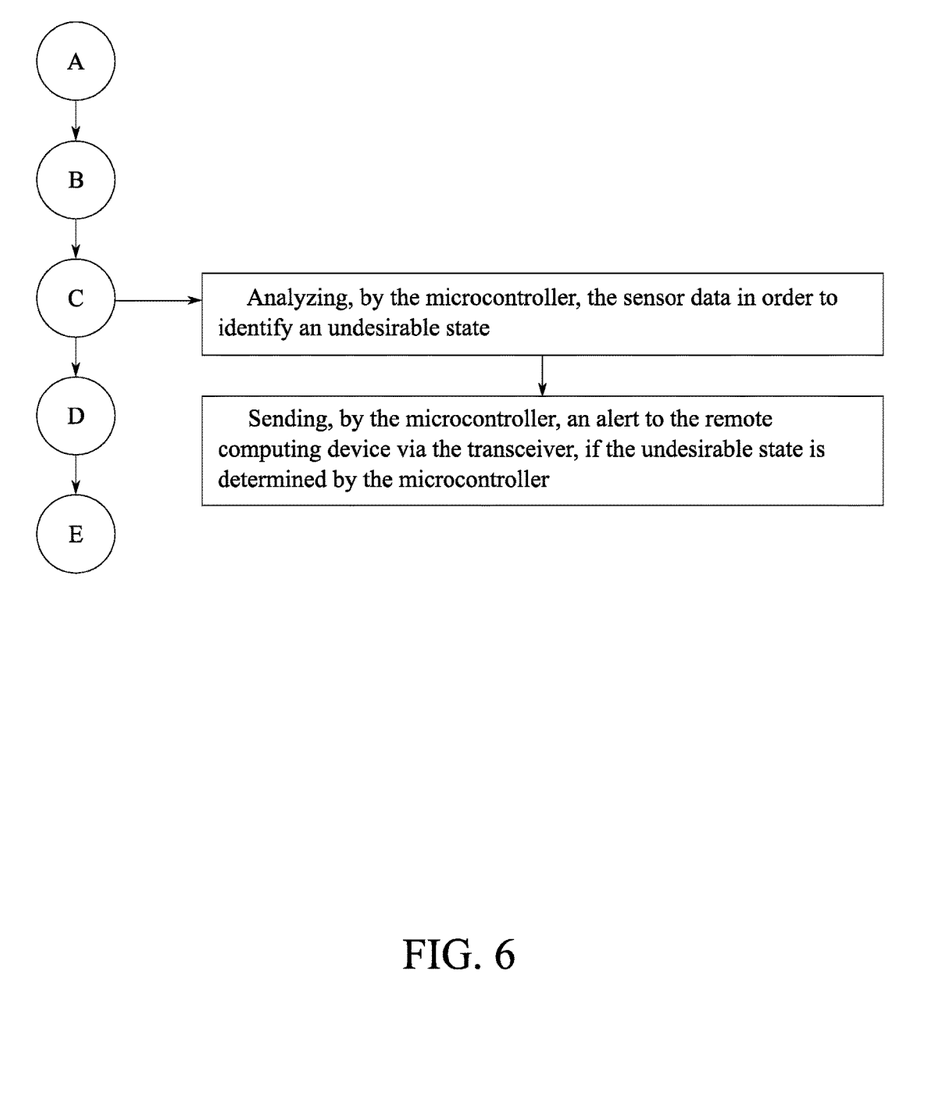
FIG. 6 is a flowchart thereof, further depicting steps for sending an alert if the microcontroller detects an undesirable state, such as an full canister, low power, a broken pressure seal, etc.

In reference to FIG. 6, the microcontroller 12 analyzes the sensor data gathered from the plurality of sensors 34 in order to identify the undesirable state. When the undesirable state is determined through a particular sensor reading or abnormalities in the sensor data, the microcontroller 12 sends the alert to the remote computing device 40 via the transceiver 14. The following provides examples of situations in which an alert may be sent from the microcontroller 12 to the remote computing device 40. If the readings from the leak detector indicates there is a leak, the microcontroller 12 will notify the user of the leak and the location of the leak. If the fluid sensor detects that a canister is full, the microcontroller 12 will alert the user to change the canister. If the low power detector notices a drop in power, the microcontroller 12 alerts the user to plug in the medical device 30, recharge the battery, etc. If the pressure sensor detects a decrease in pressure, then the microcontroller 12 can alert the user of the potential leak.

Furthermore, the microcontroller 12 can be used to notify medical officials when settings have been changed by the patient or another caregiver. This allows for remote oversight of the medical device 30 to ensure that the medical device 30 is being utilized properly.

Figure 7:
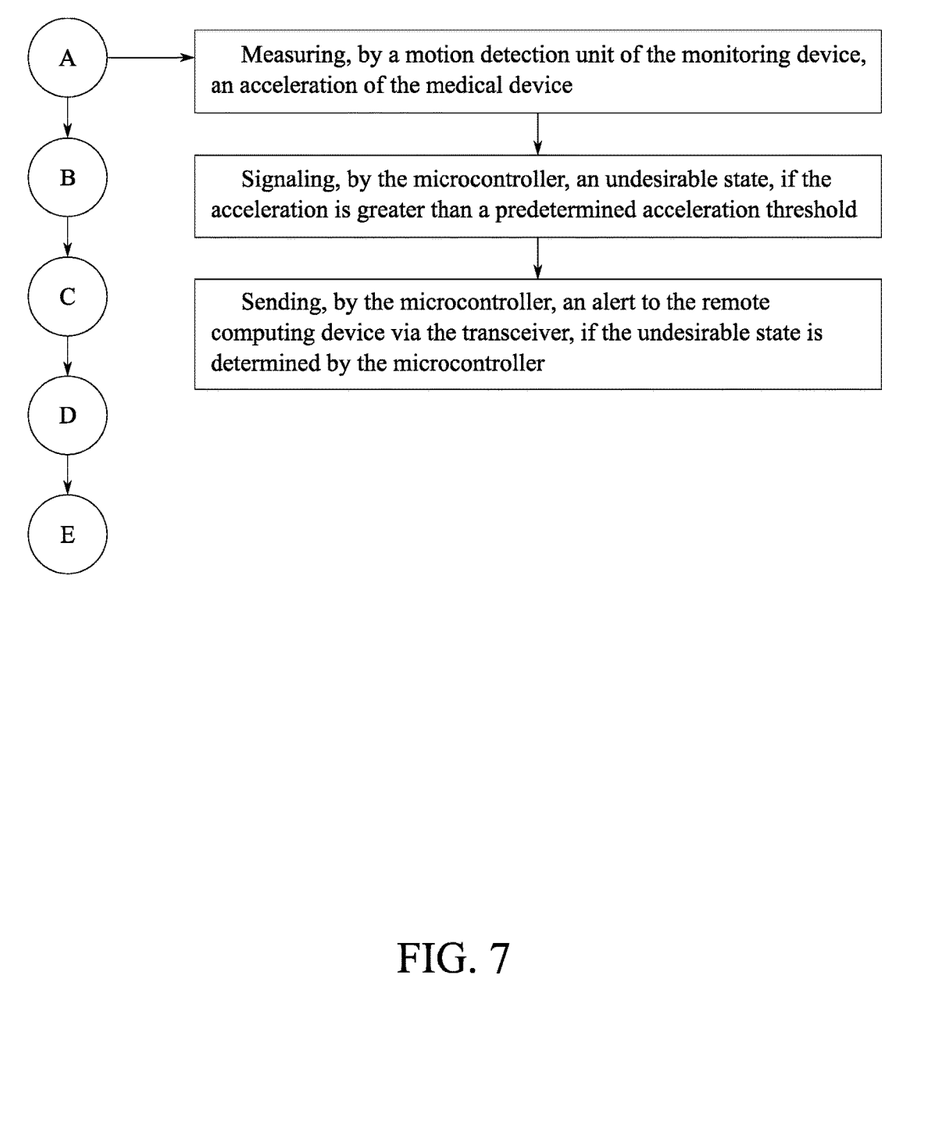
FIG. 7 is a flowchart thereof, further depicting steps for sending an alert if microcontroller detects the medical device has been dropped.

The motion detection unit 18 is used to detect if the medical device 30 has been dropped or otherwise mishandled. The motion detection unit 18 is electrically connected to the microcontroller 12 and configured to be operably disposed within or external to the medical device 30 along with the microcontroller 12. In reference to FIG. 7, the motion detection unit 18 measures an acceleration of the medical device 30 using an accelerometer, a gyroscope, or similar sensor. If the acceleration measured by the motion detection unit 18 is greater than a predetermined acceleration threshold programmed into the microcontroller 12, then the microcontroller 12 sends alerts the user through the remote communication device that the medical device 30 has been dropped or mishandled.

Figure 8:
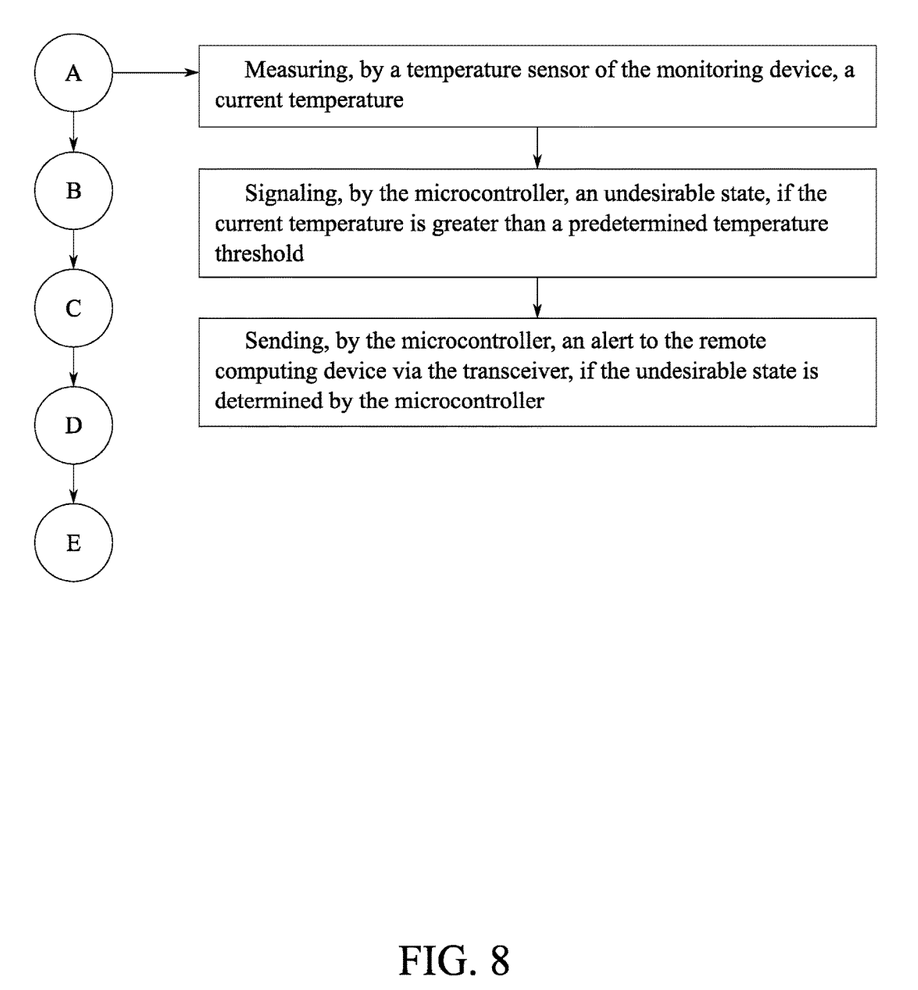
FIG. 8 is a flowchart thereof, further depicting steps for sending an alert if the microcontroller detects the medical device or the monitoring device is overheated.

Another type of alert is for the temperature of the microcontroller 12 and/or the medical device 30. In reference to FIG. 8, the temperature sensor 24 is used to measure a current temperature of the microcontroller 12 and/or the medical device 30. If the current temperature measured by the temperature sensor 24 is greater than a predetermined temperature threshold programmed into the microcontroller 12, then the microcontroller 12 sends alerts the user through the remote communication device that the medical device 30 or the monitoring device 10 is overheating. The user can then power off the device or perform other measures to cool the medical device 30 or the microcontroller 12 and prevent damage or fires.

The location detection unit 16 is electrically connected to the microcontroller 12 and is configured to be operably disposed within or external to the medical device 30. The location detection unit 16 is utilized to track the current location of the medical device 30 using positional navigation standards such as the global positioning system (GPS). This allows the user to track the location of the medical device 30 through the dashboard application to ensure the medical device 30 does not get stolen, is with the stated location of the patient, etc.

In some embodiments, the present invention may be utilized in conjunction with a new type of film drape. The drape is useful as it signifies if there is a leak or compromised seal. The drape will turn a specific color in the place of the leak, thus signifying where said leak is located. This will allow clinicians and other medical workers to quickly fix the compromised seal in an efficient and timely manner.

Figure 11:
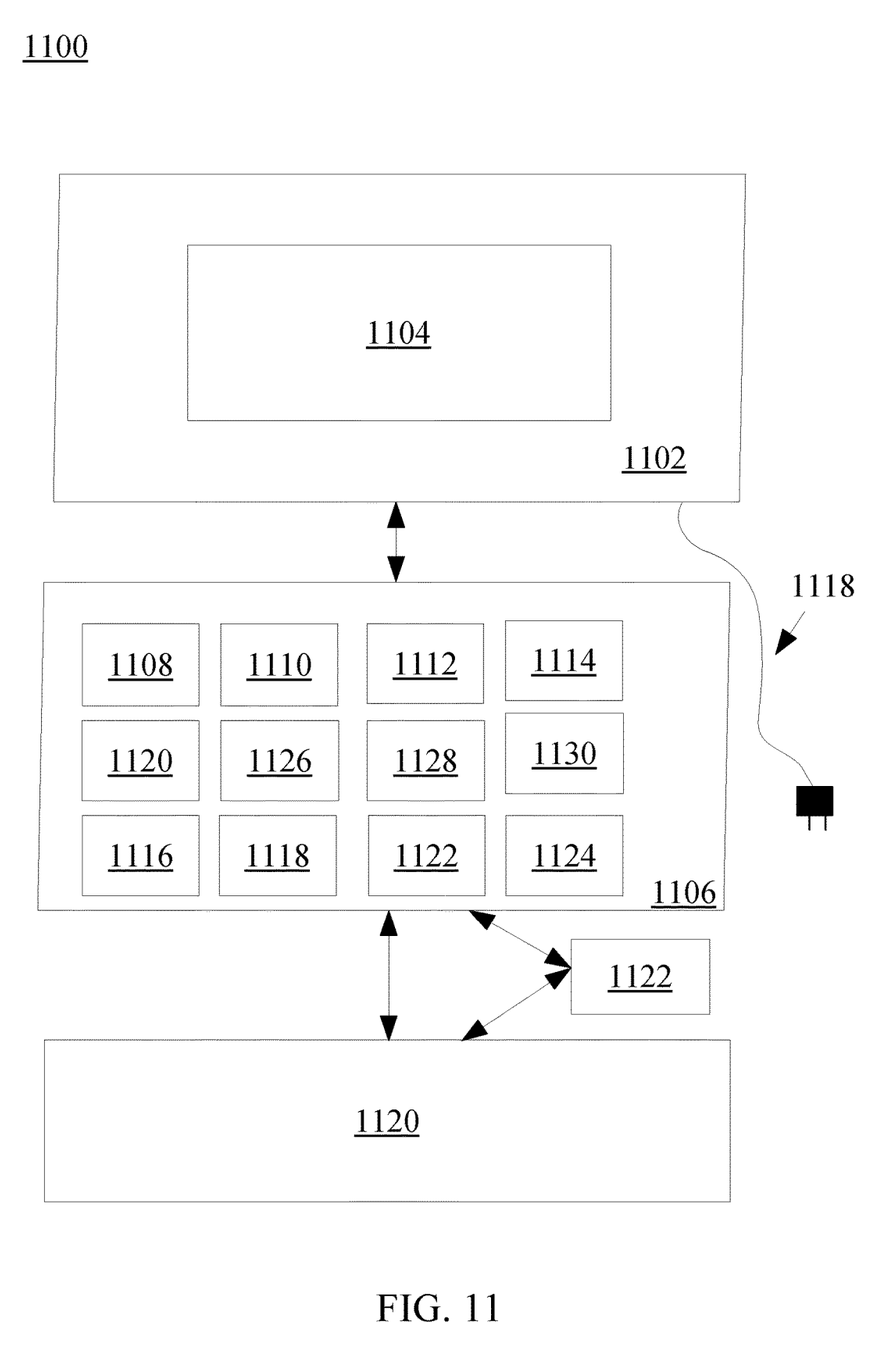
FIG. 11 is a system according to some embodiments.
Figure 12:
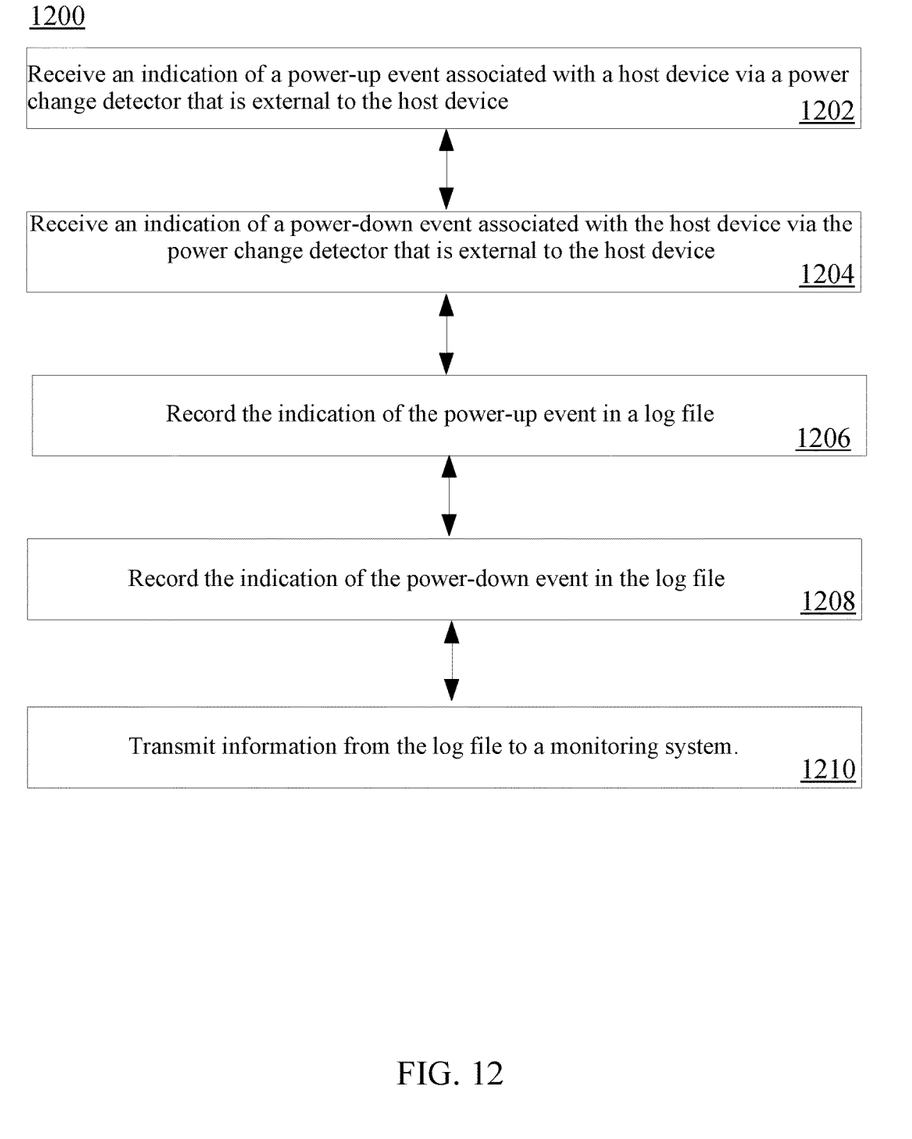
FIG. 12 is a method according to some embodiments.

FIG. 11 and FIG. 12 may relate to determining a user or patient's compliance when using a host or medical device (e.g., a NPWT unit). A patient's compliance may be measured by determining how long the host or medical device was used such as when it was turned on and when it was turned off. These events may be called power-up events and power-down events. FIG. 11 and FIG. 12 may also relate to a method of determining a location of the host device so that it may be recovered for future use because often times, host devices are loaned to users/patients for home use and users may lose or misplace the host devices.

Referring now to FIG. 11, an embodiment of a system 1100 is illustrated. The system 1100 may comprise a host device 1102, a monitoring system 1120, a monitoring device 1106 and a mobile device 1122. The mobile device 1122 may be used to send commands to the monitoring device 1106 as well as retrieve data from both the monitoring system 1120 and the monitoring device 1106.

In some embodiments, the host device 1102 may comprise a NPWT unit or another type of device such as, but not limited to, a medical device that may be used in a hospital setting, long term care center and/or may be used at home with a patient. The host device 1102 may comprise a display screen 1104 such as, but not limited to, a light emitting diode (LED) screen or a liquid crystal display (LDC) screen. The display screen 1104 may visually indicate a status of the host device 1102. For example, the display screen 1104 may indicate a power status of the host device (e.g., on or off). The host device 1102 may receive power through a power cord 1118. The power cord may comprise any gauge of wire such as, for example, 12 to 18-gauge wire. The host device 1102 and/or the monitoring device 1106 may be configured to communicate with an electronic medical records or electronic health records system.

The monitoring device 1106 may comprise, but is not limited to, the monitoring device 10 as described above. The monitoring device 1106 may include a camera 1108, a speaker 1110, a microphone 1112, a processing unit 1114, a clock 1130, a logger 1116, a transceiver 1118, a power change detector 1120, an accelerometer 1128 and a tracking device 1124.

The processing unit 1114 may comprise a microprocessor such as, but not limited to, microprocessor 12. The processing unit 1114 may comprise any commercially available Central Processing Units (CPUs) in the form of one-chip microprocessors. The processing unit 1114 may include the clock 1130 for tracking times of power-up events and power-down events. In some embodiments, the clock 1130 may comprise a separate clocking circuit that is external to the processing unit 1114. The processing unit 1114 may also communicate with a memory/storage device 1126 that stores data.

The storage device 1126 may comprise any appropriate information storage device, including combinations of magnetic storage devices (e.g., a hard disk drive), optical storage devices, solid state storage devices, remotely connected storage, and/or semiconductor memory devices. The storage device 1126 may store a program and/or processing logic for controlling the processing unit 1114. The processing unit 1114 performs instructions of the program and thereby operates in accordance with any of the embodiments described herein. For example, the processing unit 1114 may receive data such as, but not limited to, power-up events and power-down events and may store information associated with these events in the storage device 1126.

Similar to the clock 1130, the logger 1116 may be internal to, operates as part of, or may be synonymous with the processing unit 1114. In some embodiments, the logger 1116 may communicate with the clock 1130 to determine a start time and an end time associated with the aforementioned power-up and power-down events. The start and end times may be stored via the logger 1116 in the storage device 1126.

The transceiver 1118 may be configured to communicate via a wired and/or wireless communication network (not shown in FIG. 11). The transceiver 1118 may be used to communicate, for example, with one or more users or external systems to transmit data collected at the monitoring device 1106. In some embodiments, the transceiver 1118 may transmit information in one or more data packets at preset intervals such as times when a network has minimal usage or based on preset times when data should be collected and analyzed at an external system. The monitoring system 1120 may also be able to ping the monitoring device 1106 to retrieve information on demand.

The camera 1108 may comprise a digital camera for monitoring changes in the display screen 1104 to determine power-up events and power-down events. The speaker 1110 may be used to transmit various sound frequencies from the monitoring device 1106 to aid in determining a location of the monitoring device. The microphone 1112 may be used to detect various sound frequencies emitted from the host device and, as such, may also be used to determine a power-up event, power-down event or an alarm event.

The power change detector 1120 may utilize the camera 1108 and microphone 1112, as described above, but it may also determine power changes such as, but not limited to, power-up and power-down events associated with the host device based on the host device drawing more or less power by, for example, monitoring electrical flow in the power cord associated with the host device. For example, the power change detector may utilize non-contact voltage detection technology to detect a voltage in the power cord. Non-contact voltage detection technology may detect a changing magnetic field around an AC or DC energized object.

In some embodiments, the power change detector 1120 may utilize the accelerometer 1128 that may sense vibrations (or a lack of vibrations) being created by a host device. As such, the accelerometer 1128 may also be used to determine a power-up event and a power-down event. In some embodiments, the power change detector 1120 may be integrated, at least in part, with the processing unit 1114.

The tracking device 1122 may comprise an apparatus to help track a location of the host device to which the monitoring device 1106 is monitoring. In some embodiments, the tracking device 1122 may comprise a radio that transmits a signal which can be tracked by another device (e.g., a mobile device 1132 such as, but not limited to, a phone or a tablet). For example, the tracking device 1122 may track the power monitoring device using at least one of a global positioning system (GPS), a global navigation satellite system (GNSS), radio transmissions (e.g. BLUETOOTH, ZIGBY, radio frequency (RF) transmissions), and cellular triangulation methods. In some embodiments, the tracking device 1122 may utilize the speaker 1110 to transmit an audible sound to help locate the host device. For example, when retrieving a host device, a mobile device 1132 may show an approximate location of the device (e.g., a particular house or address). However, to find the host device within that address, a command may be sent to the host device to emit a distinctive sound which may make it easier to find the host device at the particular address.

In some embodiments, the tracking device may use radio transmissions associated with exchanging data between devices to facilitation determination of a location of the host device. For example, the tracking device 1122 may determine a direction of a host device based on a signal strength of a radio transmission and/or a data rate being transferred between the devices (e.g., a higher data rate indicates a closeness to the host device).

Referring now to FIG. 12, a method 1200 that may be performed by the local monitor 1106 described with respect to FIG. 11 is illustrated. The flow chart described herein does not imply a fixed order to the steps, and embodiments of the present invention may be practiced in any order that is practicable. Note that any of the methods described herein may be performed by hardware, software, or any combination of these approaches. For example, a non-transitory computer-readable storage medium may store thereon instructions that when executed by a machine or processor result in performance according to any of the embodiments described herein. In some embodiments, method 1200 may relate to a work flow for determining, and logging/recording, power-up events, power down events and alarm events associated with a host apparatus. Furthermore, the method 1200 may relate to tracking a host apparatus. At 1202, an indication of a power-up event or an alarm event associated with a host device is received. The indication may be received at a processor unit via a power change detector that is external to the host device.

For illustrative purposes, and to aid in understanding features of the specification, some examples will now be introduced. These examples are not intended to limit the scope of the claims. In a first example, a power change detector may be located in close proximity to a power cord of the host device (e.g., within a few inches). In some embodiments, the power change detector may be internal or external the monitoring device. In this embodiment, the power change detector may detect the initiation of a voltage running through the power cord of the host device. This initiation of voltage may be interpreted as a power-up event.

In a second example, a microphone may be in proximity to the host device and may detect an increase in sound being transmitted at one or more specific frequencies which may be associated with the host device. For example, the increase in sound may comprise a series of beeps or a melody that the host device transmits during power-up or an alarm event. The sound may also comprise a whirring sound at a specific frequency. The detection of the sound received by the microphone may be interpreted as a power-up event or an alarm event. In some embodiments, the microphone may be internal or external to the monitoring device. The determination of a power up event may be limited to specific frequencies or a series of sounds being received.

In yet another example, a camera may capture a change associated with a display screen that is electrically coupled with the host device. For example, in a case of an LED or LCD display, color changes may occur, the screen may brighten or writing may appear on the display screen (e.g., the words "STARTING"). The aforementioned changes may be captured by the camera and these changes may be transmitted to the processing unit which may determine that a power-up event or alarm has occurred. In some embodiments, character recognition may be used to determine a power-up event or a power-down event. However, in some embodiments, a determination may be based on determining a change in a display screen.

In another example, the host device may comprise an accelerometer that monitors vibrations. In this example, when a host device starts to vibrate, the accelerometer may detect these vibrations and an indication of vibrations may be transmitted to the processing unit where they may interpret the indication as a power-up event. In some embodiments, the accelerometer may only transmit an indication of the vibrations after a predetermined amount of time has passed (e.g., 3 seconds of constant vibration) to avoid false power-up events being reported.

At 1204, an indication of a power-down event or an alarm event associated with the host device may be received. The indication may be received at a processing unit, via the power change detector that is external to the host device. Continuing with the above examples and in the first example, the power change detector, located in proximity to the power cord of the host device, may detect the cessation of a voltage being run through the power cord associated with the host device. This voltage cessation may be interpreted as a power-down event. In the second example, the cessation of sound received at the microphone 1112 may be interpreted as a power-down event. Regarding the camera example, the camera may capture a display screen associated with the host device that has gone blank (e.g., removal of all previous indications of a power-up event) and this may be interpreted as a power-down event. Likewise, the accelerometer may detect a cessation in vibrations and this cessation of vibrations may be interpreted as a power-down event.

At 1206, the indication of the power-up event (or the alarm event) may be recorded in a log file and, at 1208, the indication of the power-down event (or the alarm event) may also be recorded in the log file. Each indication may comprise a time that each event (e.g., a time of the power-up event, alarm event or a time of the power-down event) occurred as well as a duration of each event. In some embodiments, location information may also be stored in the log file. For example, the log file may store last known GPS coordinates or a location based on a network address. Location information stored in the log file may aid in the recovery of a host device.

At 1210, information from the log file may be transmitted to a monitoring system. Transmission of the log file may comprise breaking the log file into packets and transmitting the log file via a network to the monitoring system for determining user compliance with the host device and location of the host device.

In some embodiments, the tracking device 1122 may be used store location data into the log file that is transmitted to the monitoring system.

Although the invention has been explained in relation to its preferred embodiment, it is to be understood that many other possible modifications and variations can be made without departing from the spirit and scope of the invention as hereinafter claimed.

What is claimed is:

1. A power monitoring device for monitoring events comprising:
    a processor;
    a power change detector to detect power changes in a host device wherein the power change detector monitors power being drawn by the host device based on at least one of (i) detecting power usage through an exterior of a power cord electrically coupled to the host device, (ii) receiving an image from a camera aimed at a control panel of the host device where power usage is detected based on a visual change in the received image, (iii) monitoring vibration of the host device or (iv) sound emitted by the host device;
    a logger to record, via the processor, a log of power changes detected by the power change detector in the host device; and
    a transceiver to transmit the log to a monitoring system.

2. The power monitoring device of claim 1, further comprising:
    a tracking device to track the power monitoring device using at least one of GPS, GNSS, short range radio transmissions, and cellular triangulation methods.

3. The power monitoring device of claim 2, wherein the tracking device uses radio transmissions associated with exchanging data between devices to facilitation determination of a location of the host device.

4. The power monitoring device of claim 1, wherein the logger records first information associated with a power-up event and second information associated with a power-down event.

5. The power monitoring device of claim 3, wherein the logger further records a duration associated with the power-up event and a duration associated with the power-down event.

6. The power monitoring device of claim 4, wherein the monitoring device is configured to communicate with an electronic medical records or electronic health records system.

7. The power monitoring device of claim 3, where the transmitter transmits the first information and the second information in one or more data packets at preset intervals via a network.

8. The power monitoring device of claim 1, further comprising a speaker to emit a sound to facilitate in determining a location of the host device or a microphone to record information associated with the host device.

9. A method of reporting power-up events and power-down events associated with devices, the method comprising:
    receiving an indication of a power-up event associated with a host device, at a processor, via a power change detector that is external to the host device;
    receiving an indication of a power-down event associated with the host device, at the processor, via the power change detector that is external to the host device;
    recording, via a processor, the indication of the power-up event in a log file;
    recording, via the processor, the indication of the power-down event in the log file; and
    transmitting information from the log file to a monitoring system.

10. The method of claim 9, further comprising:
    determining, via radio transmissions associated with exchanging data between devices, a location of the host device.

11. The method of claim 9, wherein the power change detector monitors power being drawn by the host device based on at least one of (i) detecting power usage through an exterior of a power cord electrically coupled to the host device, (ii) receiving an image from a camera aimed at a control panel of the host device where power usage is detected based on a visual change in the received image, (iii) monitoring vibration of the host device and (iv) sound emitted by the host device.

12. The method of claim 9, wherein a logger records first information associated with the power-up event and second information associated with a power-down event.

13. The method of claim 11, wherein the logger further records a duration associated with the power-up event and a duration associated with the power-down event.

14. The method of claim 9, where a transmitter transmits the information from the log file in one or more data packets at preset intervals via a network.

15. A non-transitory computer-readable medium containing processor executable steps that when executed by a processor, perform a method of reporting power-up events and power-down events associated with devices, the method comprising:
receiving an indication of a power-up event associated with a host device, at a processor via, a power change detector that is external to the host device;
receiving an indication of a power-down event associated with the host device, at the processor, via the power change detector that is external to the host device;
recording, via a processor, the indication of the power-up event in a log file;
recording, via the processor, the indication of the power-down event in the log file; and
transmitting information from the log file to a monitoring system.

16. The medium of claim 15, wherein the power change detector monitors power being drawn by the host device based on at least one of (i) detecting power usage through an exterior of a power cord electrically coupled to the host device, (ii) receiving an image from a camera aimed at a control panel of the host device where power usage is detected based on a visual change in the received image, (iii) monitoring vibration of the host device or (iv) sound emitted by the host device.

17. The medium of claim 15, wherein a logger records first information associated with the power-up event and second information associated with a power-down event.

18. The medium of claim 17, wherein the logger further records a duration associated with the power-up event and a duration associated with the power-down event.

19. The medium of claim 15, where a transmitter transmits the information from the log file in one or more data packets at preset intervals via a network.

20. The medium of claim 15, wherein the method further comprises:
determining, via radio transmissions associated with exchanging data between devices, a location of the host device.

* * * * *